(12) United States Patent
Manasherov et al.

(10) Patent No.: US 8,460,643 B2
(45) Date of Patent: Jun. 11, 2013

(54) FORMULATION FOR PROPHYLAXIS OF ORAL CAVITY DISEASES

(75) Inventors: Tamaz Omarovich Manasherov, Moscow (RU); Svetlana Konstantinovna Matelo, Moscow region (RU); Alexandr Vladimirovich Grosser, Moscow region (RU)

(73) Assignee: Obschestvo S Organichennoi Otvetstvennostyu "WDS", Moscow (RU)

( * ) Notice: Subject to any disclaimer, the term of this patent is extended or adjusted under 35 U.S.C. 154(b) by 877 days.

(21) Appl. No.: 11/915,334

(22) PCT Filed: Nov. 25, 2005

(86) PCT No.: PCT/RU2005/000600
§ 371 (c)(1),
(2), (4) Date: Jul. 14, 2008

(87) PCT Pub. No.: WO2006/130040
PCT Pub. Date: Dec. 7, 2006

(65) Prior Publication Data
US 2009/0041684 A1    Feb. 12, 2009

(30) Foreign Application Priority Data
May 23, 2005    (RU) ............... 2005115513

(51) Int. Cl.
*A61Q 11/00*  (2006.01)
*A61K 8/00*  (2006.01)
*A61K 8/46*  (2006.01)

(52) U.S. Cl.
USPC ............................... 424/53; 424/57

(58) Field of Classification Search
USPC ............................................. 424/53, 57
See application file for complete search history.

(56) References Cited

U.S. PATENT DOCUMENTS

| 4,206,198 A | * | 6/1980 | Schmolka | 424/49 |
| 5,603,922 A | * | 2/1997 | Winston et al. | 424/49 |
| 6,509,007 B2 | * | 1/2003 | Rajaiah et al. | 424/53 |

OTHER PUBLICATIONS

Fruit Essence Capsule. http://www.vegetableessencecapsules.com/fruit_essence_capsules.php. Accessed Mar. 16, 2011.*
Fruit Essence Capsule. http://www.vegetableessencecapsules.com/fruit_essence_capsules.php.*

* cited by examiner

*Primary Examiner* — Jeffrey S. Lundgren
*Assistant Examiner* — Chris Simmons
(74) *Attorney, Agent, or Firm* — Ladas & Parry LLP

(57) ABSTRACT

The invention relates to medicine, namely, to stomatology, in particular, to formulation for prophylaxis of oral cavity diseases. The formulation comprises: drinking water, glycerol, xylitol, silica, xanthan gum, methylparaben, propylparaben, titanium dioxide, perfume, bromelain, sodium saccharin, sodium lauryl sulfate or alkylamidobetain, calcium glycerophosphate, and magnesium chloride or glycerophosphate magnesium at following component ratio, % wt.: glycerol—20-25; xylitol—10-14; i 10 silica—22-26; xanthan gum—1.2-1.4; methylparaben—0.2-0.3; propylparaben—0.08-0.12; sodium saccharin—0.1-0.3; titanium dioxide—0.2-0.4; perfume—0.7-1.0; bromelain—0.1-0.7; sodium lauryl sulfate—1.2-1.4 or alkylamidobetain—1.2; calcium glycerophosphate—0.6-1.0; magnesium chloride—0.08-0.16 or magnesium glycerophosphate—0.16; and water—up to 100.

1 Claim, No Drawings

FORMULATION FOR PROPHYLAXIS OF ORAL CAVITY DISEASES

FIELD OF APPLICATION

The invention relates to medicine, namely, to stomatology, and concerns specifically a formulation for prophylaxis of oral cavity diseases.

BACKGROUND OF INVENTION

There are known formulations for prevention of dental caries and periodontium diseases in the form of tooth-pastes, elixirs, and tooth washes, comprising fluorides, plant extracts, minerals, perfumes, and water (RU C1 No 22204990, A61K7/16, 2003; SU C1 No 1837867, A61K7/16, 1991), tooth-paste <<Parodontol>> with green tea extract (RU C1 No 2241437, A61K7/16, 2004), tooth-pastes <<Novy Zhemchug>> (New Pearls), <<Parodontax>>.

The most close analogue to the solution proposed provides formulation for teeth and periodontium prophylaxis (RU C1 No 2188626, A61K7/16, 2002) comprising: sodium fluoride or sodium monofluorophosphate, sodium carboxymethylcellulose, titanium dioxide, sodium saccharate, sorbitol or glycerol, silica, food dye, vaseline oil, perfume and water, camomile extract, panthenol, calcium glycerophosphate, and polyvinylpyrrolidone. However, known formulation doesn't provide for good enough cleaning of teeth and their mineralization, as well as therapeutical and prophylactic effect.

SUBSTANCE OF INVENTION

Technical result of the invention proposed consists in improved teeth cleaning, maintenance of their mineralization, inhibition of bacterial dental deposits formation, as well as enhanced enamel resistivity and reduced inflammatory phenomena in periodontium.

This result is achieved with a new formulation for prophylaxis of teeth and periodontium diseases.

The proposed formulation contains following components: glycerol, xylitol, silica, xanthan gum, methylparaben, propylparaben, titanium dioxide, perfume, bromelain, sodium saccharin, sodium lauryl sulfate (alkylamidobetain), calcium glycerophosphate, magnesium chloride (magnesium glycerophosphate), and drinking water. Its distinction from known formulations lies in the use of proteolytic enzyme bromelain, obtained from pineapple stalks, natural sweetener xylitol, and magnesium chloride or magnesium glycerophosphate, which ensure superior therapeutical and prophylactic, remineralizing, pronounced anti-inflammatory, anti-deposit formation and cleaning action.

Bromelain is a group of high-molecular glycoproteins (H. R. Maurer, CMLS Cell. Mol. Life. Sci., 58 (2001), pp. 1234-1245). Bromelain is found in juice of pineapple fruits (both ripe and green), and also in the plant stalks. Fractional analysis has revealed in its composition 8 proteases. Protein hydrolysis proceeds in wide range of medium pH (3.0-8.0), thus allowing to enhance the quality of oral hygiene, and creating conditions for mineral components intake by tooth tissues.

The enzyme is actively resorbed by mucosa over the whole length of gastrointestinal tract. Bromelain possesses anti-inflammatory and immunocorrective action, which is associated with both direct proteolytic action of the enzyme and regulatory effect of its utilization products (peptide fragments). It is used for alleviating inflammatory processes in injuries, prevention of soft tissues edema, as well as for enhancement of their reconstitution after traumas and other injuries. On oral application, it reduces inflammation and edema, and accelerates tissues reparation processes. Due to the presence of protease inhibitors it is safe for viable tissues. Very low toxicity makes it suitable means for regulation of chronic inflammatory diseases. These proteases are used as food additives.

Xylite. In tooth-paste formulation this substance performs several functions: being a sweetener, xylite improves its taste properties; being a polyatomic alcohol, it acts as a water-retaining component. Mechanism of its involvement in biochemical metabolism of streptococci is characterized as lethal synthesis, resulting in reduced activity of pathogenic microorganisms and improved conditions of oral cavity organs. Xylite facilitates teeth remineralization processes. (Tanzer J. M./Xylitol chewing gum and dental caries. //Int. Dent. J., 1995 February; 45(1 Suppl 1):65-76).

Calcium glycerophosphate is a source of active phosphorus and calcium supply to teeth and periodontal tissues, which accelerates mineralization processes and improves anti-carious effect of the formulation. Besides, it enhances anabolic processes in tissues, which is important for prophylaxis of dental diseases.

Magnesium (of inorganic or organic salts) is a structural component of teeth. Magnesium is incorporated in complex formulation as microelement, which is a cofactor for phosphatases. Under the influence of these enzymes, incorporation of phosphates into solid teeth tissues increases.

Thus, highly efficient formulation has been developed for prophylaxis of dental diseases of teeth and soft oral cavity tissues, in which preparations synergistically enhance each other action. As a result of action of the proposed formulation, substantial delay in formation of soft dental deposit on all the teeth surfaces has been observed, thus creating conditions for tooth enamel saturation with mineral components of saliva, and also aiding to reduce microbial load on periodontal tissues.

REALIZATION OF INVENTION

Examples of formulation combinations are listed in Table 1.

TABLE 1

|  | Example 1 Concentration, % | Example 2 Concentration, % | Example 3 Concentration, % |
| --- | --- | --- | --- |
| Glycerol* | 20 | 22 | 25 |
| Xylitol | 10 | 12 | 14 |
| Silica | 22 | 24 | 26 |
| Xanthan gum | 1.2 | 1.3 | 1.4 |
| Methylparaben | 0.2 | 0.24 | 0.3 |
| Propylparaben | 0.08 | 0.1 | 0.12 |
| Sodium saccharin | 0.1 | 0.2 | 0.3 |
| Titanium dioxide | 0.2 | 0.3 | 0.4 |
| Perfume TP 8065 | 0.7 | 0.8 | 1.0 |
| Bromelain | 0.1 | 0.3 | 0.7 |
| Sodium lauryl sulfate | — | 1.3 | 1.4 |
| Alkylamidobetain | 1.2 | — | — |
| Calcium glycerophosphate | 0.6 | 0.8 | 1 |
| Magnesium chloride | 0.08 | 0.12 | — |
| Magnesium glycerophosphate | — | — | 0.16 |
| Drinking water | to 100% | to 100% | to 100% |

Formulations are prepared in the form of tooth-paste as follows.

1. Weigh ⅔ of glycerol quantity required. Add to it xanthan gum and calcium glycerophosphate. Mix to formation of homogeneous mass.
2. Heat the required quantity of water in measuring bin to 75-78° C., and then feed water into mixer.
3. Add to water sodium saccharate, xylitol, parabens, magnesium chloride (or magnesium glycerophosphate—in example 3). Mix to formation of transparent solution.
4. Add glycerol suspension of components (see point 1.1) to the solution obtained. Mix to formation of homogeneous mass.
5. Degas and mix for 10 minutes to full deaeration of the mixture.
6. Add titanium dioxide into mixer.
7. Degas and mix for 10 minutes to the full deaeration of the mixture.
8. Add silica into mixer.
9. Degas and mix for 30-40 minutes.
10. Homogenize tooth-paste with homogenizing pump for 15-20 minutes.
11. Cool tooth-paste down to 40-45° C. with mixing.
12. Add bromelain to the rest of glycerol and mix until formation of homogeneous mass.
13. Feed bromelain suspension in ⅓ glycerol into mixer and mix for 20 minutes until formation of homogeneous mass.
14. Add perfume and sodium lauryl sulfate (or amidopropylbetain in example 1).
15. Mix paste for 30 minutes until formation of homogeneous mass.

Method of manufacturing and sequence of operations have been the same in all formulation examples.

Use formulation for teeth brushing two times daily for 2-3 minutes.

The proposed formulation has been used by volunteers as hygienic means possessing therapeutic and prophylactic action in order to evaluate its hygienic and anti-inflammatory action.

Clinical studies of the tooth-paste included:
studies of cleaning action,
studies of anti-inflammatory effect,
determination of possible allergenic and locally irritating action.

Studies have been conducted for three months by a blind scheme, with stomatologist-epidemiologist conducting dental survey not knowing to which group each patient belongs.

Clinical studies included 10 people aged 27 to 42 years. All adults have voluntarily agreed to participate in said studies.

Before studies, dental status had been evaluated for all the participants. The clinical investigation consisted of 4 series of tooth-paste tests. Each series comprised preliminary two-week use of identical tooth-paste of the "Colgate maximum caries protection" type and 14-days testing of studied tooth-pastes samples, which were given out to test persons in a random order.

The studies comprised:
examination of solid and soft tissues of oral cavity: lips, tongue, hard and soft palate, teeth and gums;
determination of hygienic state in oral cavity by PHP index (Podshadley A. G., Haley P., 1968);
evaluation of periodontal tissues state by gingivitis index (IG) (Loe H., Silness J. 1963) indicating localization and severity of gingivitis.

Examinations have been conducted 5 to 6 hours after teeth brushing.

Changes in hygienic index of studies participants are presented in Table 2.

TABLE 2

| | Nos. of formulations studied | | |
|---|---|---|---|
| | Formulation 1 | Formulation 2 | Formulation 3 |
| Initial state (M ± m) | 2.43 ± 0.42 | 2.62 ± 0.42 | 2.60 ± 0.53 |
| Examination No. 2 (M ± m) | 2.05 ± 0.40 | 2.27 ± 0.36 | 2.02 ± 0.35 |
| Examination No. 3 (M ± m) | 1.55 ± 0.37 | 1.77 ± 0.27 | 1.51 ± 0.35 |
| Examination No. 4 (M ± m) | 1.43 ± 0.35 | 1.59 ± 0.40 | 1.32 ± 0.39 |
| Examination No. 5 (M ± m) | 1.40 ± 0.41 | 1.38 ± 0.38 | 1.40 ± 0.26 |
| Examination No. 6 (M ± m) | 1.38 ± 0.28 | 1.34 ± 0.32 | 1.37 ± 0.32 |
| Examination No. 7 (M ± m) | 1.42 ± 0.18 | 1.37 ± 0.25 | 1.29 ± 0.25 |
| Examination No. 8, day 14 (M ± m) | 1.45 ± 0.16 | 1.36 ± 0.26 | 1.12 ± 0.21 |
| Effectiveness (%) | 40.3 | 48.1 | 56.9 |

Investigations of tooth-paste containing 0.7% bromelain have demonstrated that the initial values of hygienic PHP index in studies' participants amounted to 2.60±0.53, corresponding to unsatisfactory level of oral cavity hygiene. Results of subsequent examinations have revealed reliable improvement in hygienic condition of oral cavity in studies' participants, with PHP index diminishing towards the end of investigations to 1.12±0.21 (p<0.02). Cleaning effectiveness of the tooth-paste over the period of use amounted to 56.9%.

Similar trend had been observed also in studies of cleaning properties of the tooth-paste containing bromelain 0.3%. During its use, value of hygienic index has reliably decreased from 2.62±0.42 to 1.36±0.26 (p<0.02). Cleaning effectiveness of this sample amounted to 48.1%.

Studies of cleaning properties of the paste containing bromelain 0.1% have revealed that values of hygienic index decrease in a similar manner, but to a lesser extent. This index amounted to 40.3%.

Changes in gingivitis index in participants of the studies are listed in Table 3.

TABLE 3

| Group | Formulation 1 | Formulation 2 | Formulation 3 |
|---|---|---|---|
| Initial state (M ± m) | 1.11 ± 0.11 | 1.16 ± 0.21 | 1.13 ± 0.12 |
| Examination No. 2 (M ± m) | 0.98 ± 0.07 | 0.99 ± 0.15 | 1.01 ± 0.08 |
| Examination No. 3 (M ± m) | 0.93 ± 0.08 | 0.96 ± 0.14 | 0.89 ± 0.19 |
| Examination No. 4 (M ± m) | 0.88 ± 0.12 | 0.89 ± 0.12 | 0.70 ± 0.14 |
| Examination No. 5 (M ± m) | 0.84 ± 0.13 | 0.82 ± 0.15 | 0.83 ± 0.12 |
| Examination No. 6 (M ± m) | 0.81 ± 0.11 | 0.81 ± 0.12 | 0.94 ± 0.11 |
| Examination No. 7 (M ± m) | 0.77 ± 0.14 | 0.75 ± 0.11 | 0.95 ± 0.09 |
| Examination No. 8, day 14 (M ± m) | 0.79 ± 0.14 | 0.71 ± 0.12 | 0.92 ± 0.14 |
| Effectiveness (%) | 28.8 | 38.8 | 18.6 |

Initial state of periodontal tissues in persons participating in the IG index test corresponds to a mild or medium severity gingivitis. Values of gingivitis index at initial examinations: 1.13±0.12 in the first series, 1.16±0.21 in the second series, and 1.11±0.11 in the third one. Reduction in inflammatory events rate in periodontal tissues amounted to 18.6% when using the tooth-paste with maximum bromelain concentration; 38.8% when using the tooth-paste with bromelain concentration 0.3%; and 28.8%, when using the paste containing bromelain 0.1%, correspondingly.

By subjective estimate of the majority of participants, a substantial delay had been observed in apparent dental deposit formation on frontal teeth during period of use of the proposed tooth-paste formulation, as well as prolonged retention of teeth smoothness on lingual surfaces (in a number of reports, 24 hours and more). Besides, those persons who clean regularly side teeth surfaces with a dental floss, have pointed out to a sharp decrease in the amount of dental deposits on side areas of teeth when using tooth-pastes with bromelain concentrations 0.3% and 0.7%, in comparison with that containing bromelain 0.1% and Colgate paste.

Of special merit is the fact that during wash-out period a substantial deterioration had been observed both of hygienic index and indices characterizing periodontium condition.

Evaluation of the proposed tooth-paste formulation effects on dental enamel condition had been performed in comparison with a tooth-paste having sodium fluoride concentration 0.15% in terms of F⁻ (Blend-a-Med tooth-paste) by acid enamel biopsy. Studies have been conducted for one month, with weekly control of the index determined by procedure described below. Sampling had been performed on the intact surfaces of frontal teeth. Each test group included 30 people from among typical production users.

Acid enamel biopsy method according to V. K. Leontjev and V. A. Distel' (1975), comprising application of strictly determined quantity of demineralizing liquid on the enamel, its sampling after a certain period of time and subsequent determination of calcium content in acid demineralisate, allows to determine rate of acidic solubility of enamel. Quantitative analysis of calcium content in acidic biopsy material is performed by spectrophotometry.

Test results are presented in Table 4.

Acid enamel biopsy results indicate to the strengthening of dental enamel structure. Reduction in calcium and phosphorus recovery in biopsy material indicate to the increase in acid and chemical resistivity of enamel, testifying to its hardening. During four weeks of the studies, as a result of using the proposed tooth-paste formulation, calcium recovery with acid decreases by 20.53% with bromelain concentration 0.3%, and 20.71% with bromelain concentration 0.1%, whereas corresponding indicator in test persons brushing teeth with Blend-a-Med paste amounted to 11.95%, indicating to high remineralizing potential of the proposed tooth-paste formulation.

TABLE 4

|  | Formulation 1 | Formulation 2 | Blend-a-med tooth-paste |
| --- | --- | --- | --- |
| Before | Ca 113.25; P 56.1 | Ca 113.25; P 55.0 | Ca 91.2; P 46.0 |
| 1 week | Ca 112.25; P 50.5 | Ca 110.20; P 50.8 | Ca 90.0; P 42.5 |
| 2 week | Ca 92.8; P 47.7 | Ca 99.25; P 48.3 | Ca 85.2; P 40.5 |
| 1 month | Ca 89.7; P 44.9 | Ca 90.0; P 45.7 | Ca 80.3; P 39.2 |
| Reduction in enamel solubility, % | Ca 20.79; P 19.96 | Ca 20.53; P 16.91 | Ca 11.95; P 14.7 |

Therefore, proposed formulation allows to attain technical result comprising improvement in teeth brushing, delay in the formation of dental deposit, enhancement of teeth remineralization, as well as increase in enamel resistivity and reduction of inflammatory events in periodontal tissues.

The invention claimed is:

1. A composition in the form of a toothpaste for prophylaxis of oral cavity diseases and for cleaning and mineralization of tooth surfaces, the composition consisting of
glycerol; xylitol as a natural sweetener; silica; xanthan gum; methylparaben; propylparaben; sodium saccharin; titanium dioxide; perfume; bromelain as a proteolytic enzyme; sodium lauryl sulfate or alkylamidobetain; calcium glycerophosphate; magnesium chloride or magnesium glycerophosphate; and water at the following weight percentages for each component:
glycerol from 20 to 25%;
xylitol from 10 to 14%;
silica from 22 to 26%;
xanthan gum from 1.2 to 1.4%;
methylparaben from 0.2 to 0.3%;
propylparaben from 0.08 to 0.12%;
sodium saccharin from 0.1 to 0.3%;
titanium dioxide from 0.2 to 0.4%;
perfume from 0.7 to 1.0%;
bromelain from 0.1 to 0.7%;
sodium lauryl sulfate from 1.2 to 1.4% or alkylamidobetain at 1.2%;
calcium glycerophosphate from 0.6 to 1.0%;
magnesium chloride from 0.08 to 0.16% or magnesium glycerophosphate at 0.16%; and
water up to 100%.

* * * * *